(12) United States Patent
Haraldsson et al.

(10) Patent No.: US 7,514,096 B2
(45) Date of Patent: *Apr. 7, 2009

(54) TRIACYLGLYCEROLS OF ENRICHED CLA CONTENT

(75) Inventors: Gudmundur G. Haraldsson, Reykjavik (IS); Asgeir Saebo, Eidsnes (NO); Carl Skarie, Detroit Lakes, MN (US); Daria Jerome, Detroit Lakes, MN (US)

(73) Assignee: Aker Biomarine ASA (NO)

( * ) Notice: Subject to any disclaimer, the term of this patent is extended or adjusted under 35 U.S.C. 154(b) by 637 days.

This patent is subject to a terminal disclaimer.

(21) Appl. No.: 10/623,825

(22) Filed: Jul. 21, 2003

(65) Prior Publication Data

US 2004/0018225 A1 Jan. 29, 2004

Related U.S. Application Data

(63) Continuation of application No. 09/160,416, filed on Sep. 25, 1998, now abandoned, and a continuation-in-part of application No. 09/132,593, filed on Aug. 11, 1998, now Pat. No. 7,078,051, which is a continuation-in-part of application No. 09/042,538, filed on Mar. 17, 1998, now abandoned, and a continuation-in-part of application No. 09/042,767, filed on Mar. 17, 1998, now Pat. No. 6,015,833.

(51) Int. Cl.
*A61K 31/201* (2006.01)
(52) U.S. Cl. .................... 424/439; 514/558; 514/560
(58) Field of Classification Search .................. None
See application file for complete search history.

(56) References Cited

U.S. PATENT DOCUMENTS

| | | | |
|---|---|---|---|
| 2,242,230 A | 5/1941 | Burr | 260/398 |
| 2,350,583 A | 6/1944 | Bradley | 260/195.6 |
| 3,162,658 A | 12/1964 | Baltes et al. | 260/405.6 |
| 3,278,567 A | 10/1966 | Rathien et al. | 260/405.6 |
| 3,729,379 A | 4/1973 | Emken | 195/30 |
| 4,164,505 A | 8/1979 | Krajca | 260/405.6 |
| 4,381,264 A | 4/1983 | Struve | 260/405.6 |
| 5,017,614 A | 5/1991 | Pariza et al. | 514/558 |
| 5,070,104 A | 12/1991 | Pariza et al. | 514/549 |
| 5,208,356 A | 5/1993 | Pariza et al. | 554/79 |
| 5,288,619 A | 2/1994 | Brown et al. | 435/134 |
| 5,428,072 A | 6/1995 | Cook et al. | 514/560 |
| 5,430,066 A | 7/1995 | Cook et al. | 514/558 |
| 5,468,887 A | 11/1995 | Gupta | 554/169 |
| 5,554,646 A | 9/1996 | Cook et al. | 514/560 |
| 5,585,400 A | 12/1996 | Cook et al. | 514/560 |
| 5,674,901 A | 10/1997 | Cook et al. | 246/452 |
| 5,725,873 A | 3/1998 | Cook et al. | 424/442 |
| 5,760,082 A | 6/1998 | Cook et al. | 514/560 |
| 5,760,083 A | 6/1998 | Cook et al. | 514/560 |
| 5,804,210 A | 9/1998 | Cook et al. | 424/440 |
| 5,814,663 A | 9/1998 | Cook et al. | 514/560 |
| 5,827,885 A | 10/1998 | Cook et al. | 514/558 |
| 5,851,572 A | 12/1998 | Cook et al. | 426/2 |
| 5,855,917 A | 1/1999 | Cook et al. | 424/502 |
| 5,856,149 A | 1/1999 | Pariza et al. | 435/134 |
| 5,885,594 A | 3/1999 | Nilsen et al. | 424/401 |
| 5,986,116 A | 11/1999 | Iwata et al. | 554/126 |
| 6,015,833 A * | 1/2000 | Saeboe et al. | 514/558 |
| 6,184,009 B1 | 2/2001 | Cain et al. | 435/134 |
| 7,029,691 B1 * | 4/2006 | Saebo et al. | 424/439 |

FOREIGN PATENT DOCUMENTS

| | | |
|---|---|---|
| AU | 253031 | 7/1964 |
| EP | 779033 A1 | 6/1997 |
| EP | A-0839897 | 10/1997 |
| EP | A-EPO97307110 | 12/1997 |
| EP | 0902082 A1 | 8/1998 |
| EP | 0950410 | 12/2000 |
| GB | 558881 | 1/1944 |
| WO | WO90/09110 | 8/1990 |
| WO | WO97/18320 | 11/1991 |
| WO | WO 96/34855 | 11/1996 |
| WO | WO 96/38137 | 12/1996 |
| WO | WO97/46320 | 3/1997 |
| WO | WO 97/18320 | 5/1997 |
| WO | WO 9718320 A1 * | 5/1997 |
| WO | WO 97/37546 | 10/1997 |
| WO | WO 97/46118 | 12/1997 |
| WO | WO 97/46230 | 12/1997 |
| WO | WO 98/05318 | 2/1998 |
| WO | WO 98/05319 | 2/1998 |
| WO | WO 98/49129 | 11/1998 |
| WO | WO 01/44485 A | 6/2001 |
| WO | WO 01/53512 A | 7/2001 |

OTHER PUBLICATIONS

R.O. Adlof et al., Changes in Conjugated Linoleic acid Composition Within Samples Obtained from a Single Source, Lipids, vol. 36, No. 3, 2001, pp. 315-317.*
Cowan, "Isomerization and Trans-Esterifiation," *JAOCS* 72:492-99 (1950).
Christie et al., "Isomers in Commercial Samples of Conjugated Linoleic Acid," *JAOCS* 74 (11):1231 (1997).
Kepler et al., *J. Biol. Chem.* 241:1350-54 (1966).

(Continued)

*Primary Examiner*—Michael G. Hartley
*Assistant Examiner*—Nabila Ebrahim
(74) *Attorney, Agent, or Firm*—Casimir Jones, S.C.

(57) ABSTRACT

Novel acylglycerides are disclosed comprising mono-, di- and triacylglycerides characterized by predominantly containing the conjugated linoleic acids t9,c11- and c10,t12 octadecadienoic acids to the exclusion of 11,13-, 8,10- and trans, trans isomers.

2 Claims, 2 Drawing Sheets

OTHER PUBLICATIONS

W. Parodi, *J. Nutr.* 127(6):1055-60 (1997).
Belury, "Conjugated Dienoic Linoleate; A Polyunsaturated Fatty Acid with Unique Chemoprotective Properties," *Nut. Rev*, 53(4):83-9 (1995).
Ha et al., *Cancer Res.*, 50:1097 (1991).
Birt et al., *Cancer Res.*, 52:2035-s (1992).
Ip, *Am. J. Clin. Nutr*, 66(6):1523s (1997).
Sehat et al., Lipids 33(2):217-21 (1998).
Jie, et al., "High-Resolution Nuclear Magnetic Resonance Spectroscopy—Amplification to Fatty Acids and Triacyglycerols," *Lipids* 32 (10): 1019-34 (1997).
Scholfield and Koritalia, "A Simple Method for Preparation of Methyl trans-10,cis-12 Octadecadienoate," *JOACS* 47(8):303 (1970).
Ron Udell, Information About Conjugated Linoleic Acid, published by Soft Gel Technologies Incorporated.
Sugano et al., "Conjugated Linoleic Acid Modulates Tissues of Chemical Mediators and Immunoglobulins in Rats," *Lipids*, 33(5):521-27 (1998).
Matreya Catalog, 1997, pp. 33-34.
Selin CLA Product Literature, Jan. 1997.
Hudtwalcker & Co. AS Technical Data Sheet, exact publication date unknown.
Lipid Technology Newsletter, Peter J. Barnes, Ed., vol. 4, No. 5, pp. 85-86 (Oct. 1998).
Natural Lipids Ltd, AS Technical Data Sheet, Jan. 20, 1997.
Theil et al., "Conjugated Linoleic Acid Improves Performance and Body Composition in Swine," Iowa State University,Midwest Animal Sciences Meeting, Abstract 127:61 (1998).
Quinn et al., "A Comparison of Modified Tall Oil and Conjugated Linoleic Acid on Growing-Finishing Pig Growth Performance and Carcass Characteristics," Kansas State University and Lonza, Inc., Midwest Animal Sciences Meeting, Abstracat 128:61 (1998).
Dugan et al., "The Effect of Conjugated Linoleic Acid on Fat to Lean Repartitioning and Feed Conversion in Pigs," *Canadian Journal of Animal Science* 77:723-725 (1997).
Shantha et al., "Conjugated Linoleic Acid Concentrations in Processed Cheese Containing Hydrogen Donors, Iron and Dairy—Based Additives," *Food Chemistry* 47:257-261 (1993).
Bradley et al., "Alkali-Induced Isomerization of Drying Oils and Fatty Acids," *Ind. Eng. Chem.* 34(2):237-242 (1942).
Jie et al., "Synthesis and Nuclear Magnetic Resonance Properties of All Geometrical Isomers of Conjugated Linoleic Acids," *Lipids* 32(10):1041-1044 (1997).
Arcos et al., "Rapid Enzymatic Production of acylglycerols from conjugated linoleic acid and glyerol in the solvent-free system,"*Biotechnology Letters* 20:617 (1998).

Holman et al., "Unusual Isomeric Polyunsaturated Fatty Acids in Liver Phospholipids of Rats Fed Hydrogenated Oil," *PNAS* 88:4830-34 (1991).
Radlove et al., "Catalytic Isomerization of Vegetable Oils," *Ind. Eng. Chem.* 38(10):997-1002 (1946).
Sebedio et al., "Linoleic Acid Isomers in Heat Treated Sunflower Oils," *JAOCS* 65(3):362-366 (1988).
Sebedio et al., "Metabolites of Conjugated Isomers of Linoleic Acid (CLA) in the Rat," *Biochem. Biophys. Acta.* 1345;5-10 (1997).
Chin et al., "Dietary Sources of Conjugated Dienoic Isomers of Linoleic Acids, a Newly Recognized Class of Anticarcinogens," *J. Food. Comp. Anal.* 5:185-197 (1992).
Park et al., "Effect of Conjugated Linoleic Acid on Body Composition in Mice," *Lipids* 32(8):853-58 (1997).
Berdeau et al., "A Simply Method of Preparation of Methyl *trans*-10, *cis*-12- and *cis*-9, *trans*-11-Octadecadienoates from Methyl Linoleate," *JAOCS* 75:1749-1755 (1998).
Haraldsson et al., "The Preparation of Concentrates of Eicosapentaenoic Acid And Docosahexaenoic Acid By Lipase-Catalyzed Transesterification of Fish Oil With Ethanol," *JAOCS* 74:1419-1424 (1997).
Haraldsson et al., "The Synthesis Of Homogeneous Triglycerides of Eicosapentaenoic Acid and Docosahexaenoic Acid by Lipase," *Tetrahedron* 51;941-952 (1995).
Haroldsson et al., "Studies on the Positional Specificity of Lipase from *Mucor meihei* during Interesterification Reactions of Cod Liver Oil with *n*-3 Polyunsaturated Fatty Acid and Ethyl Ester Concentrates," *Acta Chemica Scandinavica* 45:723-730 (1991).
Banni et al., J. of Lipid Research 42;1056 (2001).
Chuang et al., Lipids 36:139 (2001).
Bretillon et al., Lipids 34;965 (1999).
Janssen et al., Biomedical And Environmental Mass Spectrometry 16;1-6 (1988).
Park et al., Lipids 34:235-241 (1999).
Sebedio et al., Lipids 34:1319-1325 (1999).
Zambell et al., Lipids 35;777-782 (2000).
Blankson et al., American Society for Nutritional Sciences 1-6 (2000).
Yurawecz et al., Lipid 8;277-282 (1999).
Communication of Notices of Opposition.
Sehat et al, Improved Separtation of Conjugated Fatty Acid Methyl Esters by Silver Ion-High-Performance Liquid Chromatography, Lipids, vol. 34, No. 4, 1999, 407-413 (In particular: p. 409, Figure 2).
Report on Experiments.
GC analytical data.
Mylnefield Research Services Limited Report.
T848/03.

* cited by examiner

TRIACYLGLYCEROLS OF ENRICHED CLA CONTENT

RELATED APPLICATIONS

This is a Continuation of application(s) Ser. No. 09/160,416 filed on Sep. 25, 1998 now abandoned which is a continuation-in-part of Ser. No. 09/042,538, filed on Mar. 17, 1998 now abandoned, Ser. No. 09/042,767, filed on Mar. 17, 1998 now U.S. Pat. No. 6,015,833 and Ser. No. 09/132,593, filed on Aug. 11, 1998 now U.S. Pat No. 7,078,051.

FIELD OF THE INVENTION

This invention relates to novel triacylglycerols containing greater than 50 percent conjugated linoleic acids, upwardly in excess of 80 percent of the c9,t11-octadecadienoic and t10,c12 octadecadienoic isomers in a mixture, with less than five percent each of 8,10-octadecadienoic acyl-, 11,13-octadecadienoic acyl-glycerol isomers, and various trans, trans-octadecadienoic acyl isomers.

BACKGROUND OF THE INVENTION

In animal lipid metabolism, there are certain fatty acids, termed "essential" fatty acids, which must be supplied from vegetable sources. The essential fatty acids are required as structural components for the lipid content of cell membranes but cannot be synthesized by the animal, as summarized in Ohlrogge, et al., *The Plant Cell* 7: 957 (1895). This includes the essential fatty acid c9,c12-linoleic acid. Structural variants of 9,12-linoleic acid, some of which are naturally occurring, include the conjugated isomers.

The biological activity associated with conjugated linoleic acids (termed CLA) is diverse and complex. At present, very little is known about the mechanisms of action, although several preclinical and clinical studies in progress are likely to shed new light on the physiological and biochemical modes of action. The anticarcinogenic properties of CLA have been well documented. Administration of CLA inhibits rat mammary tumorigenesis, as demonstrated by Ha, et al., Cancer Res., 52: 2035s (1992). Ha, et al., Cancer Res., 50: 1097 (1990) reported similar results in a mouse forestomach neoplasia model. CLA has also been identified as a strong cytotoxic agent against target human melanoma, colorectal and breast cancer cells in vitro. A recent major review article confirms the conclusions drawn from individual studies. See Ip, Am. J. Clin. Nutr., 66 (6 Supp): 1523s (1997).

Although the mechanisms of CLA action are still obscure, there is evidence that some component(s) of the immune system may be involved, at least in vivo. U.S. Pat. No. 5,585,400 (Cook, et al.) discloses a method for attenuating allergic reactions in animals mediated by type I or TgE hypersensitivity by administering a diet containing CLA. CLA in concentrations of about 0.1 to 1.0 percent was also shown to be an effective adjuvant in preserving white blood cells. U.S. Pat. No. 5,674,901 (Cook, et al.) disclosed that oral or parenteral administration of CLA in either free acid or salt form resulted in elevation in CD-4 and CD-8 lymphocyte subpopulations associated with cell-mediated immunity. Adverse effects arising from pretreatment with exogenous tumor necrosis factor could be alleviated indirectly by elevation or maintenance of levels of CD-4 and CD-8 cells in animals to which CLA was administered. Finally, U.S. Pat. No. 5,430,066 describes the effect of CLA in preventing weight loss and anorexia by immune stimulation.

Apart from potential therapeutic and pharmacologic applications of CLA as set forth above, there has been much excitement regarding the use of CLA nutritively as a dietary supplement. CLA has been found to exert a profound generalized effect on body composition, in particular redirecting the partitioning of fat and lean tissue mass. U.S. Pat. No. 5,554,646 (Cook, et al.) discloses a method utilizing CLA as a dietary supplement in which pigs, mice, and humans were fed diets containing 0.5 percent CLA. In each species a significant drop in fat content was observed with a concomitant increase in protein mass. It is interesting that in these animals, increasing the fatty acid content of the diet by addition of CLA resulted in no increase in body weight, but was associated with a redistribution of fat and lean within the body. Another dietary phenomenon of interest is the effect of CLA supplementation on feed conversion. U.S. Pat. No. 5,428,072 (Cook, et al.) provided data showing that incorporation of CLA into animal feed (birds and mammals) increased the efficiency of feed conversion leading to greater weight gain in the CLA supplemented animals. The potential beneficial effects of CLA supplementation for food animal growers is apparent.

In the development of a defined commercial source of CLA for both therapeutic and nutritional applications, a process for generating large amounts of defined material is needed. The problem with most CLA products made by conventional approaches is their heterogeneity, and substantial variation in isoform from batch to batch. Considerable attention has been given to the fact that the ingestion of large amounts of hydrogenated oils and shortenings, instead of animal tallow, has resulted in a diet high in trans-fatty acid content. For example, Holman, et al., PNAS, 88:4830 (1991) showed that rats fed hydrogenated oils gave rise to an accumulation in rat liver of unusual polyunsaturated fatty acid isomers, which appeared to interfere with the normal metabolism of naturally occurring polyunsaturated fatty acids. These concerns were summarized in an early Editorial in Am. J. Public Health, 84: 722 (1974) Therefore, there exists a strong need for a CLA biologically active product of defined composition.

In the typical animal or human diet, most fatty acids are not provided in free fatty acid form, but rather in phosph- or acyl-glyceride form. The general type and distribution of fatty acid containing lipid components in plant tissue is described in detail in Ohlrogge, et al., supra. For many feed and food applications it is desirable to present the fatty acids in their acylglycerol form. The uptake and metabolism pathways and kinetics differ from the acylglyceride and free acid forms. Most importantly, the binding, rheology, and palatability properties of these respective compounds differs. True triacylglycerols are considerably more palatable, with markedly reduced aftertaste.

There are chemical processes which effect the acylation of a glycerol backbone with fatty acids of straight chain structure. Generally, the first and third hydroxyl positions of the glycerol molecule are derivatized first, and finally the second position is acylated. Reaction to completion is difficult, and selection of conditions able to drive the reaction to saturation, result in double bond rearrangements and transacylation events giving rise to a fatty acid moiety content differing from the distribution of the original preparation.

An alternative to chemical methods of forming triacylglycerol is the use of enzymes such as various lipases. It is found that fatty acids or esters derived therefrom, and glycerol are quite efficiently reacted under very mild conditions in the presence of solid phase bound lipases. WO 91/16443 discloses a method utilizing *C. antarctica* lipase, *C. fugosa* lipase, and other enzymes to catalyze formation of triacylglycerides from free polyunsaturated fatty acids or their esters and glycerol. Conversion to glycerides is essentially complete at 98 percent when the resulting water or lower polyhydric alcohol byproducts are continuously removed. Maintenance of isomer distribution is also reported in Haraldsson, et al., *Tetrahedron* 51: 941 (1995). Again, these results are applicable only to the higher polyunsaturated fatty acids and esters. The degree of reaction, and the influence of chain length and double bond portions on enzyme specificity is discussed in detail in Macrae, *Biochemical Soc. Trans.* 17: 1146 (1989). An overview of the industrial use of lipases is set forth in Vukson, "Industrial Applications of Lipases", and Kotting, et al., "Lipases and Phospholipases in Organic Synthesis", in Paul Woolley and Steffen Petersen (eds.), *Lipases: Their Structure, Biochemistry & Application* (1994). For the use of lipases in transesterifizing fatty acids to alternate glycerol positions, see Haraldsson, et al. *JAOCS* 74: 1418 (1997).

SUMMARY OF THE INVENTION

A preferred form of CLA incorporates free fatty acids of the derived conjugated linoleic fatty acids or their corresponding esters into acylglycerols of either mono-, di-, or triacylglycerol structure. Several advantages are realized by utilizing CLA in this form. First, the triglyceride is much more stable to oxidation than the esters or free fatty acids, so that the product shelf-life and storage potential is much enhanced. Secondly, the triglyceride>diglyceride>monoglyceride is increasingly fat miscible with increasing CLA acylation. Often, especially in animal feeds, other lipid products as a source of energy may conveniently be provided in conjunction with CLA glycerides to achieve the derived nutritive benefits of the CLA together with a balanced ration. These rations may be compounded as premixes.

In the present composition, a high percentage of linoleic acid or its corresponding ester are converted primarily to the conjugated c9,t11 and t10,c12 isomers in a carefully controlled reaction yielding greater than 90 percent of these isomers, so that less than a combined 1 percent of the 11,13 isomers, less than 1 percent of the 8,10 isomers, less than 1 percent of the double trans species (the t9,t11 and t10,t12 isomers), and less than 1 percent total unidentified linoleic acid species, in the aggregate less than five percent, is present in contrast to conventional compositions. In many individual product runs, the final composition has levels of these species virtually undetectable by GC analysis. The 1 percent limit in concentration of the 11,13 and 8,10 isomers serves as a convenient and practical quality assurance standard of purity for a commercial scale manufactured food grade product. In the method of the present invention, CLA or esters thereof such defined composition are then reacted with glycerol in the process of lipase, preferably *C. antarctica* lipase, to produce acylglycerol derivatives. The percentage of mono-, di-, and tri-glycerides is dependent upon the time of reaction.

In the present invention, a triacylglyeride is provided having a biological effect, and comprising the structure

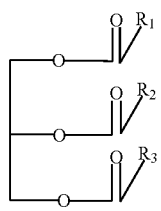

wherein $R_1$, $R_2$ and $R_3$ are selected from a hydroxyl group and a C18:2 fatty acid in which the C18:2 fatty acid is characterized in the content of c9,t11-octodecadienoic acid; and t10, c12-octodecadienoic acid. There conjugated fatty acids are present in greater than 50 percent, with a content of 8,10-octodecanoic acid and 11,13-octodecanoic acid isomers of less than 5 percent in the aggregate. The content of trans, trans isomers is also typically less than 5 percent. The acylglycerides may be used either in triglyceride form or as mono- or diglyceride intermediates in animal feed or food at a level of about 0.05 to about 3.0 percent by weight.

The present invention also provides a new process for making novel conjugated linoleic acid-containing compositions from free fatty acids of the requisite purity and defined composition. The process comprises the steps of dissolving in the specific non-aqueous solvent propylene glycol, an alkali compatible with a non-aqueous medium such as potassium hydroxide, cesium hydroxide, cesium carbonate, or an organic alkali such as tetraethyl ammonium hydroxide, in the absence of metallic-based isomerization catalyst systems, blending into the alkaline propylene glycol a seed oil, heating under an inert gas atmosphere and at ambient pressures to a temperature in the range of 130-165 degrees C., preferably about 150 degrees C. under nonreflux conditions, separating the fatty acid fraction by acidification, and optionally further purifying and dehydrating by vacuum molecular distillation and/or centrifugation. Optionally, the process stream may be interrupted after the reaction mix is prepared, either prior to or after the heat step. The mix may then be stored for further processing in continuous acidification and distillation steps and/or be further processed at another location. After heating to effect isomerization, the isomerized blended reaction mix contains 30-60 percent processed seed oil, 10-40 percent alkali, and 30-60 percent propylene glycol. In this process it is important to utilize propylene glycol because of its heating properties and the patterns of isomerization obtained. The components of the dissolved fatty acid reaction mix are present, as follows:

| | |
|---|---|
| 30-60 | percent seed oil |
| 10-40 | percent alkali |
| 30-60 | percent propylene glycol |

Thus, in the preferred method embodiment, the process comprises forming a blended reaction mix containing linoleic acid-containing seed oil, propylene glycol, and an alkali compatible with a nonaqueous medium, isomerizing said linoleic acid contained in said seed oil by heating to form conjugated linoleic acids, aquefying to release glycerol. Toxicity is avoided, as will be posed if other, undesirable organic solvents such as ethylene glycol are used. Under the nonreflux conditions, it is possible to vary the processing temperature over a range to obtain the desired result with oils of differing fatty acid composition. The temperature is critical, as the percentage of trans,trans species, as well as other undesired and unidentified species increases as temperature rises. The processing time requires about 2 to 6.5 hours and gives isomerized yields of greater than 90 percent, frequently as high as 99.5 percent. In the present process, use of sunflower and safflower oil is essential because of its high native 9,12 linoleic acid content, but also because of low levels of sterols, contaminating phospholipids, and other residues that tend to foul the processing equipment and result in a less pure final product. This makes it possible to prepare on an industrial scale, a product of controlled isomer content without a subsequent distillation step to ensure sufficient product purity.

Alternatively, the fatty acid esters may be prepared by conventional techniques, and then isomerized in a monohydric alcohol solvent in the presence of an alkali metal oxide, sodium ethoxide being preferred, according to the method more fully disclosed in co-pending application Ser. No. 09/132,593. The isomer distribution of CLA is essentially the same as with propylene glycol. The glycerol acylating step is then carried out as before.

DETAILED DESCRIPTION OF THE PREFERRED EMBODIMENT

Figure 1:
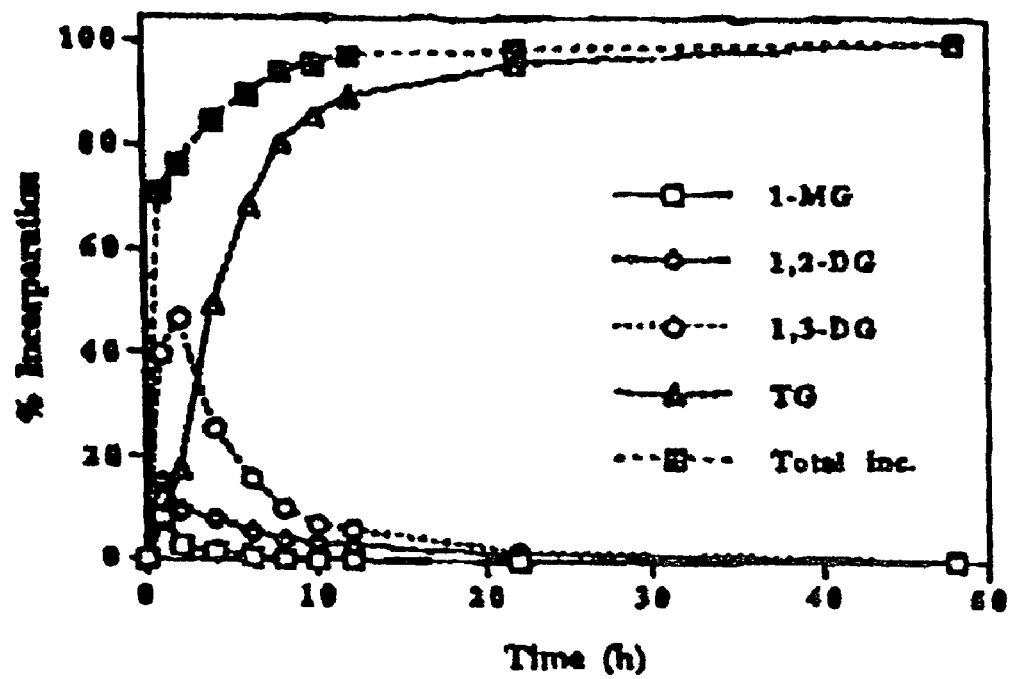
FIG. 1 is a rectilinear plot showing incorporation of CLA into various glycerides direct progress of the direct esterification reaction.
Figure 2:
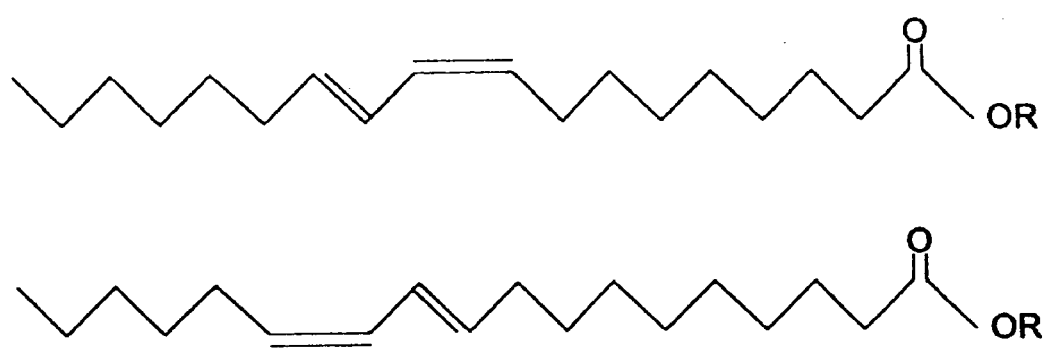
FIG. 2 is a molecular diagram of the c9,t11-octadecadienoic acid and t10,c12-octadecadienoic acid isomers.

The composition of the present invention results from a highly controlled isomerization process, under nonaqueous conditions (propylene glycol solvent for free fatty acid, and monohydric alcohol for the corresponding esters), and from using the preferred starting material of sunflower or safflower oil. This composition has not heretofore been obtained, for application to an industrial scale, because the conventional processes historically produce conjugated linoleic acids for entirely different purposes, namely, as drying oils in the paint industry. Also, there has not been an appreciation of the implications of the isomer content of the final product, because the analytical methods for characterizing the fatty acids has not been widely available.

In the older isomerization processes for the free acid, some of which are still in use in more modern format, production of the conjugated fatty acids was carried out in aqueous alkali (generally NaOH) at high temperatures in excess of 200 degrees C. and usually at superatmospheric pressures. For example, U.S. Pat. No. 2,350,583 (Bradley) discloses an aqueous alkali process utilizing treated soaps in which both conjugation and polymerization occurred under rather harsh conditions at 200 to 250 degrees C. for a period of several hours. The fractions of drying oil, starting with linseed oil, were obtained by distillation. See also Br. Patent No. 558,881 for a very similar process. In a variation of the process, U.S. Pat. No. 4,381,264 teaches a process where a low water content reaction zone (0.5% water) contains stoichiometric base in the presence of $SO_2$ to obtain conjugation of the double bonds of various polyunsaturated fatty acids. The aqueous alkali process was adapted in U.S. Pat. No. 4,164,505 to a continuous flow process in which an alkali metal hydroxide and water are continuously charged in a flow zone maintained at between 200 and 370 degrees C. At these temperatures, the time of reaction should be greatly foreshortened, but there is relatively little control over the isomerization. At the higher end of the temperature range, one would predict almost complete conversion to double trans species.

Methods of producing CLA using various nonaqueous solvents and catalysts have been described in the literature. Burr (U.S. Pat. No. 2,242,230) discloses the use of solvents such as methanol, butanol, ethanol and glycol in combination with various catalysts. These reaction parameters are summarized in Table 1. With the exception of glycol, the reactions were conducted either under reflux conditions or in sealed tubes. These reaction conditions result in imprecise control of two of the important reactions parameters identified by the Inventors—temperature and pressure. Imprecise control of these reactions parameters is likely to lead to less than complete conjugation and the formation of undesirable isomers.

TABLE 1

Patent 2,242,230

| Solvent | Catalyst | Temperature | Time |
| --- | --- | --- | --- |
| Ethanol | KOH, NaOH | reflux or higher* | varied |
| Butanol | KOH, NaOH | reflux or higher* | varied |
| Glycol | KOH | 195° C. | varied |
| Isoamyl Alcohol | KOH | reflux or higher* | varied |
| Butanol | Tributylamine | 140-175° C. | 22 hours |
| Butanol | Potassium Acetate | 175° C. | 36 hours |
| Butanol | Trisodium Phosphate | 175° C. | 36 hours |
| Butanol | Potassium Phosphate | 175° C. | 36 hours |
| Butanol | Sodium Benzoate | 175° C. | 36 hours |
| Butanol | Potassium Thiocyanate | 175° C. | 36 hours |
| Butanol | Borax | 175° C. | 36 hours |

Likewise, Baltes et al., (U.S. Pat. No. 3,162,658) disclose the use of nonaqueous solvents and various metallic bases as catalysts for the conjugation of fatty acids. The various reaction parameters of the methods described by Baltes et al. are summarized in Table 2. Baltes et al. also disclose the use various low boiling point solvents. As most of these reactions were conducted at temperatures above the boiling point of the solvent employed, it is apparent that the reactions were conducted under pressure, which is an independent factor influencing the formation of octadecadienoic acid isomers. The product derived from these reactions will thus contain undesirable isomers.

TABLE 2

Patent 3,162,658

| Solvent | Catalyst | Temperature | Time |
| --- | --- | --- | --- |
| Methanol | KOH | 60-140° C. | variable |
| Methanol | Potassium Methylate | 140° C. | variable |
| Butanol | Potassium Methylate | 140° C. | variable |
| Ethanol | Potassium Methylate | 140° C. | variable |
| Isopropanol | Potassium Methylate | 120-140° C. | variable |
| Heptane/ 3° Butanol | Potassium Butylate | reflux | variable |
| 3° Butanol | Cesium Butylate | 140° C. | variable |
| Ethylene Diamine | Potassium Methylate | 140-160° C | variable |
| Methanol | Sodium Amide | 140° C. | variable |

The CLA of the present invention lacks isomers such as the 8,10 isomer, the 11,13 isomer, and the various trans-trans isomers. This composition was produced by a tightly controlled nonaqueous alkali isomerization process. Sunflower oil or safflower oil are reacted at an ambient pressure under an inert gas atmosphere with an excess of alkali in a high-boiling point solvent, namely propylene glycol at a temperature below the boiling point of the solvent. These reaction conditions allow for precise control of the temperature (and constant ambient pressure) of the conjugation process. Preferably the alkali is an inorganic alkali such as potassium hydroxide, cesium hydroxide, cesium carbonate or an organic alkali such as tetraethyl ammonium hydroxide. The catalyst is preferably provided in a molar excess as compared to the fatty acid content of oil. The solvent is propylene glycol. Preferably, the reaction is conducted within a temperature range 130 to 165° C., most preferably at about 150° C. The time of the reaction may vary, however, there is an increased likelihood of the formation of undesirable isomers when the reaction is conducted for long periods of time. A relatively short reaction time of 2.0 to 6.5 hours has proved satisfactory for excellent yields.

The essential oils for conjugation are sunflower and safflower oil. As compared to soybean oil, these oils have lower concentrations of undesirable components such as phosphatides and sterols. These undesirable components may contribute to the formation of gums which foul the conjugation equipment and other undesirable polymers. Various properties of these oils are summarized in Tables 3, 4, and 5.

Comparison of Contaminants

TABLE 3

Phosphatides

| Soybean | 1.5-3.0% |
|---|---|
| Sunflower | .4-1% |
| Sunflower | .4-1% |

TABLE 4

Sterols (unsaponifiables by percent)

| Soybean | | Sunflower | | Sunflower | |
|---|---|---|---|---|---|
| Campesterol | 20* | Campesterol | 8 | Campesterol | 13 |
| Stigmasterol | 20 | Stigmasterol | 8 | Stigmasterol | 9 |
| β-Sitosterol | 53 | β-Sitosterol | 60 | β-Sitosterol | 52 |
| $\Delta^5$ Avensterol | 3 | $\Delta^5$ Avensterol | 4 | $\Delta^5$ Avensterol | 1 |
| $\Delta^7$ Stigmasterol | 3 | $\Delta^7$ Stigmasterol | 15 | $\Delta^7$ Stigmasterol | 15 |
| $\Delta^7$ Avenasterol | 1 | Avenasterol | 4 | Avenasterol | 3 |
| Percentage of 0.36% total in oil | | 0.36 percent total 0.36% | Total | *May not equal 100 0.36% | |

TABLE 5

| | Soybean | Sunflower | Sunflower |
|---|---|---|---|
| Iodine Value | 134.6 | 135.4 | 143.6 |
| Saponification value | 190.7 | 190.6 | 190.3 |
| Unsaponification value | .6 | .7 | .6 |

TABLE 6

Incorporation of CLA into Various Types of Glycerides During the Esterification of CLA with Glycerol.

| Time | % Incorporation | | | | Residual |
|---|---|---|---|---|---|
| h | 1-MG | 1, 2-DG | 1, 3-DG | TG | FFA % |
| 0 | 0 | 0 | 0 | 0 | 100 |
| 1 | 8.3 | 15.2 | 39.4 | 7.8 | 29.3 |
| 2 | 2.7 | 9.3 | 46.5 | 17.4 | 24.1 |
| 4 | 1.7 | 7.9 | 25.4 | 49.4 | 15.5 |
| 6 | 0.5 | 5.2 | 16.0 | 68.1 | 10.1 |
| 8 | 0.0 | 3.9 | 9.9 | 80.5 | 5.7 |
| 10 | 0.0 | 3.0 | 7.0 | 85.8 | 4.2 |
| 12 | 0.0 | 2.7 | 5.6 | 89.2 | 2.5 |
| 22 | 0.0 | 1.0 | 1.4 | 95.8 | 1.8 |
| 48 | 0.0 | 0.0 | 0.0 | 100 | 0.0 |

In the esterification of fatty acids to the alkyl esters, methanol or ethanol are preferred, although other branched or straight chain monohydric alcohols may be used. The longer the aliphatic chain of the alkyl group, the more lipid compatible the material becomes. Also the viscosity tends to increase. For different types of feed or food, whose consistency varies, product of varying viscosity can be used to obtain the desired flow or compounding characteristics without affecting the therapeutic or nutritional properties arising from the CLA moieties. The theory and practice of esterification are conventional. A basic explanation of the most common methods is set forth in the McCraw-Hill Encyclopedia of Science & Technology, McGraw-Hill Book Co., New York: 1996 (5th ed.). The animal and human body has a variety of esterases, so that the CLA-ester is cleaved to release the free fatty acids readily. Tissue uptake may have a different kinetics depending on the tissue involved and the benefit sought.

In the isomerization step, it was found that alcoholate catalysis produced a much superior product than aqueous alkali mediated isomerization. The latter process always produced undesirable isomers even under mild reaction conditions. The milder conditions do give lower amounts of unwanted isomers, but at the great expense of yield, as shown in the Examples. In most systems the appearance of the c9,t11 and t10,c12 isomers dominates and they are formed in roughly equimolar amounts. It has not heretofore been possible to control the isomerization of the one isomer to the exclusion of the other. While it is desirable to increase the percentage of one or the other isomer (depending on the physiological effect to be achieved), at present this must largely be carried out by adding an enriched source of the desired isomer.

Crude sunflower or safflower oil is the essential fatty acid source for producing CLA. Sunflower oil contains a high amount of linoleic acid (about 65% on average). Safflower oil typically contains even higher amounts (greater than 70%). Preferably, a hexane extract of crude, non-degummed oil is the starting substrate for CFAP production. This extract is commercially available and is the same quality as the oil used as the starting point for edible products. The ability to use raw sunflower or safflower oil as the starting substrate provides an important advantage because it is less expensive than refined sunflower oil.

In the process of the present invention, a novel triacylglycerol is synthesized comprising the novel CLA isomer mixture disclosed hereinafter for non-aqueous isomerization of linoleic acid from sunflower and/or safflower oils. The pure triacylglycerols highly enriched for CLA (90-96 percent) may be confirmed by H NMR. Esterification proceeds using immobilized *Candida antarctica* Lipase. Preferably, the CLA will contain at least 40 and upwardly 45-48 percent of c9,t11-octadecadienoic and t10,c12-octadecadienoic acids, and mixtures thereof. There will be less than one percent esters 8,10; 11,13; and trans, trans isomers or less than five percent in the aggregate. The resultant triacylglycerol is not purified further to remove all levels of phosphatidyl and sterol residues. But those levels remaining from isomerization of sunflower and safflower oils will be adequate for commercial applications involving safe, edible products in feed and food.

The immobilized *Candida antarctica* lipase is to be employed in a manner similar to that described for n-3 type polyunsaturated fatty acids, in Harraldson et al. The esterification reaction is conducted at 50°-75° C., preferably 65° C., in the absence of any solvent and a vacuum employed in order to remove the co-produced water or alcohols (from esters) upon formation. This shifts the triacylglycerol production to completion and ensures a highly pure product virtually free of any mono- and diacylglycerols in essentially quantitative yields. Stoichiometric amounts of free fatty acids may be used, i.e. 3 molar equivalents as based on glycerol or 1 molar equivalent as based on number of mol equivalents of hydroxyl groups present in the glycerol moiety. Only 10% dosage of lipase as based on total weight of substrates is needed, which can be used a number of times. This is very important from the productivity point of view. All this, together with the fact that no solvent is required, renders this process a high feasibility from the scaling-up and industrialization point of view, since the cut in volume and bulkiness is enormous. Also, a slight excess (<5/5) of free fatty acids may be used in order to speed up the reaction toward the end and ensure a completion of the reaction. The direct esterification reaction is demonstrated in Scheme 1.

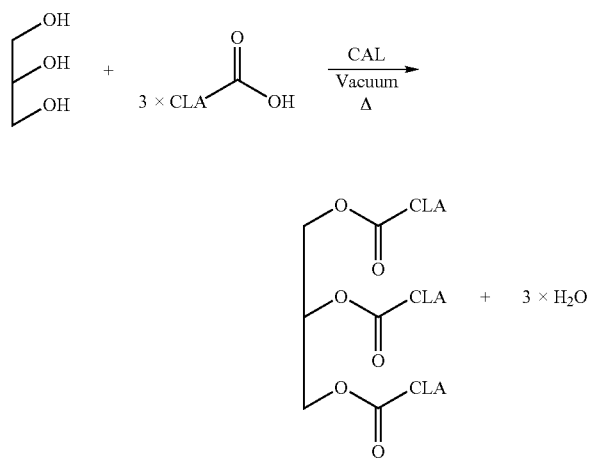

wherein R is hydrogen or an alkyl radical such as an ethyl, methyl, butyl, isopropyl, isobutyl or the like.

At the initiation of the reaction, the 1- or 3-mono-acyglyeride is formed first, followed by the 1, 3 diacylglyeride, and finally the triglyceride at the more extended reaction times. The mono- and diacylglyerides are useful intermediates in that they manifest biological activity, but have greater solubility in aqueous cellular environments and can participate in alternative molecular synthetic pathways such as synthesis of phospholipids or other functional lipids. In contrast, triglycerides are frequently deposited intact in cell membranes or storage vesicles. Thus, the administration of CLA in mono-, di- or triglycerol form rather than free fatty acid or ester, may influence the mode and distribution of uptake, metabolic rate and structural or physiological role of the CLA component.

EXAMPLE 1

General. H nuclear magnetic resonance spectra were recorded on a Bruker AC 250 NMR spectrometer in deuterated chloroform as a solvent. HPLC separations were carried out by a PrepLC™ System 500A instrument from Waters using the PrepPak® 500/Silica Cartridge column from Millipore, eluting with 10% diethyl ether in petroleum ether. Analytical GLC was conducted on a Perkin-Elmer 8140 Gas Chromatograph according to a previously described procedure, as described in Haraldsson, et al., Acta Chem Scanned 45: 723 (1991).

The immobilized *Candida antarctica* lipase was provided by Novo Nordisk in Denmark as Novozyme™. It was used directly as provided in the esterification experiments. Analytical grade diethyl ether purchased from Merck was used without any purification, but synthetic grade n-hexane also from Merck was freshly distilled prior to use in extractions and HPLC chromatography. Glycerol (99%) was purchased from Sigma and Aldrich Chemical Company and used without further purification. The CLA concentrate was provided by Natural Lipids in Norway as free fatty acids as Tonalin™. Its purity was confirmed by analytical GLC and high-field NMR spectroscopy which revealed some glyceride impurities. The CLA concentrate was found to contain 43.3% 9-cis, 11-trans-linoleic acid, 44.5% 10-trans, 12-cis-linoleic acid, 5.4% of other CLA isomers, 5.6% oleic acid and 0.6% each of palmitic and stearic acid as determined by GLC at the Science Institute.

EXAMPLE 2

The Preparation of Triacylglycerols of CLA by Direct Esterification.

Immobilized *Candida antarctica* lipase (1.25 g) was added to a mixture of glycerol (1.22 g. 13.3 mmol) and CLA as free fatty acid (M.wt.280.3 g/mol; 11.6 g, 41.5 mmol). The mixture was gently stirred on a magnetic stirrer hot plate at 65° C. under continuous vacuum of 0.01-0.5 Torr. The volatile water produced during the progress of the reaction was continuously condensed into liquid nitrogen cooled traps. After 48 h the reaction was discontinued, n-hexane added and the enzyme separated off by filtration. The organic phase was treated with an alkaline aqueous solution of sodium carbonate to remove excessive free fatty acids (when required). The organic solvent (after drying over anhydrous magnesium sulfate when appropriate) was removed in vacuo on a rotary evaporator followed by high-vacuum treatment to afford the virtually pure product as a slightly yellowish oil (10.9 g; average M.wt.878.6 g/mol; 93% yield). When stoichiometric amounts of free fatty acids were used, titration by standardized sodium hydroxide was applied to determine the free fatty acid content of the crude reaction product (less than 1% free fatty acid content as based on number of mol of ester groups, corresponding to at least 99% incorporation, which is equivalent to the minimum of 97% triglyceride content). The crude product was directly introduced into HPCL eluting with 10% diethylether in n-hexane to afford 100% pure triglyceride as a colourless oil. 250 MHz 1H NMR (CDC13) δ (ppm) 6.35-6.23 (3H, ddt, Jtrans=15.0 Hz, J=10.9 Hz, Jallyl=1.3, =CHCH=CH), 5.98-5.90 (3H, dd, Icis=10.9, J=10.9, —CH=CHCH=), 5.71-5.59 (3H, dtd, Jtrans=15.0 Hz, J=6.9 Hz, J=6.9 Hz, J=2.2 Hz, =CH=CHCH2-), 5.35-5.26

(4H, m, =CH2CH=CH— and —CH2C—ICH2-), 4.33-4.26 (2H, dd, Jgem=11.9 Hz, J=4.3, —CH2CHCH2-), 4.18-4.10 2H, dd, Jgem=1.8 Hz, J=6.0, —CH2CHCH2-), 2.37-2.31 (6H, t, J=7.4 H2, —CH2COOR), 2.19-2.05 (12H, m, —CH2CH=CH—), 1.66-1.60 (6H, qu., J=Hz, —CH2CH2COOR), 1.43-1.30 (18H, m, —CH2-), 0.91-0.86 (9H, t, J=6.7 Hz, —CH3). 13C-NMR (CDC13): 8 (ppm) 173.2, 172.8, 134.6, 130.0, 128.6, 125.5, 68.8, 62.0, 34.0, 32.9, 31.6, 29.6-28.9 (6C), 27.6, 24.8, 22.5, 14.1.

In order to monitor the progress of the reaction and provide more details about the composition of individual glycerides during the reaction, samples were collected regularly as the reaction proceeded. They were analyzed by HNMR spectroscopy and provided a good insight into the composition of mono-, di- and triacylglycerols during the progress of the reaction. The results are demonstrated in Table 6 below. As can be noticed from the table, 1,3-diacylglycerols dominated the reaction mixture during the first two hours of the reaction. After 4 hours triacylglycerols took over and had reached 98% composition after 22 hours and 100% after 48 hours. As would be expected 1,2-diacylglycerols reached considerably lower levels than the 1,3-diacylglycerols. 1-monoacylglycerols reached a maximum during the first hour of the reaction, but 2-monoacylglycerols were not detected throughout the reaction. The results showing the kinetics are plotted in FIG. 1.

What is claimed is:

1. An acylglyceride mixture comprising the structure:

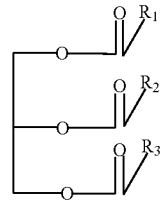

wherein $R_1$, $R_2$, and $R_3$ are selected from the group consisting of a hydroxyl group and a c18:2 fatty acid, said acylglyceride mixture comprising at least one c18:2 fatty acid moiety selected from the group consisting of c9,t11-octadecadienoic acid; and t10, c12-octadecadienoic acid, wherein said mixture has a c9,t11-octadecadienoic and t10,c12-octadecadienoic acid content of greater than 50%, and a content of less than 1% 8,10-octadecadienoic acid and less than 1% 11,13 octadecadienoic acid isomers.

2. The acylglycerides of claim 1 wherein said acylglycerides are triacylglycerides.

* * * * *